US00PP19169P2

(12) United States Plant Patent
Eskelund

(10) Patent No.: US PP19,169 P2
(45) Date of Patent: Sep. 2, 2008

(54) ROSE PLANT NAMED 'EVERA160'

(50) Latin Name: *Rosa hybrida*
Varietal Denomination: Evera160

(75) Inventor: Rosa Eskelund, Fåborg (DK)

(73) Assignee: Roses Forever ApS, Fäborg (DK)

( * ) Notice: Subject to any disclaimer, the term of this patent is extended or adjusted under 35 U.S.C. 154(b) by 0 days.

(21) Appl. No.: 11/784,551

(22) Filed: Apr. 6, 2007

(51) Int. Cl.
*A01H 5/00* (2006.01)

(52) U.S. Cl. ..... Plt./119

(58) Field of Classification Search ..... Plt./119
See application file for complete search history.

*Primary Examiner*—Annette H Para
(74) *Attorney, Agent, or Firm*—C. A. Whealy

(57) ABSTRACT

A new and distinct cultivar of Rose plant named 'Evera160', characterized by its upright and rounded plant habit; dark green-colored leaflets; freely branching growth habit; freely flowering habit; large double orange-colored flowers; flowers held upright on strong and erect peduncles; and good postproduction longevity.

1 Drawing Sheet

Botanical designation: *Rosa hybrida.*
Cultivar denomination: 'Evera160'.

BACKGROUND OF THE INVENTION

The present Invention relates to a new and distinct cultivar of Rose plant, botanically known as *Rosa hybrida,* commercially used as a potted Rose, and hereinafter referred to by the name 'Evera160'.

The new Rose is a product of a planned breeding program conducted by the Inventor in Fåborg, Denmark. The objective of the breeding program was to develop new uniform potted Rose varieties with novel and attractive flower colors, disease resistance and excellent postproduction longevity.

The new cultivar originated from a cross-pollination made by the Inventor on Mar. 1, 2004 of a proprietary Rose selection identified as code number 03-0906, not patented, as the female, or seed, parent with an unnamed Rose selection, not patented, as the male, or pollen, parent. The cultivar Evera160 was discovered and selected by the Inventor on Feb. 10, 2005 as a single flowering plant within the progeny of the stated cross-pollination in a controlled environment in F522 borg, Denmark.

Asexual reproduction of the new Rose by cuttings at Fåborg, Denmark since Dec. 1, 2005, has shown that the unique features of this new Rose are stable and reproduced true to type in successive generations of asexual reproduction.

SUMMARY OF THE INVENTION

The following traits have been repeatedly observed and are determined to be the unique characteristics of 'Evera160'. These characteristics in combination distinguish 'Evera160' as a new and distinct cultivar:

1. Upright and rounded plant habit.
2. Dark green-colored leaflets.
3. Freely branching growth habit.
4. Freely flowering habit.
5. Large double orange-colored flowers.

6. Flowers held upright on strong and erect peduncles.
7. Good postproduction longevity.

Plants of the new Rose differ from plants of the parent selections in the following characteristics:

1. Plants of the new Rose and the parent selections differ in plant habit.
2. Plants of the new Rose and the parent selections differ in flower color.

Plants of the new Rose can be compared to plants of the Rose cultivar Evera 105, disclosed in U.S. Plant Pat. No. 16,918. In side-by-side comparisons conducted in Fåborg, Denmark, plants of the new Rose differed from plants of the cultivar Evera 105 in the following characteristics:

1. Plants of the new Rose had shorter internodes than plants of the cultivar Evera 105.
2. Plants of the new Rose had larger leaf stipules than plants of the cultivar Evera 105.
3. Plants of the new Rose had more petals per flower than plants of the cultivar Evera 105.
4. Plants of the new Rose and the cultivar Evera 105 differed in flower color as plants of the cultivar Evera 105 had salmon orange-colored flowers.
5. Plants of the new Rose had longer peduncles than plants of the cultivar Evera 105.
6. Plants of the new Rose had more stamens and pistils per flower than plants of the cultivar Evera 105.

BRIEF DESCRIPTION OF THE PHOTOGRAPHS

The accompanying colored photographs illustrate the overall appearance of the new Rose, showing the colors as true as it is reasonably possible to obtain in colored reproductions of this type. Colors in the photographs may differ slightly from the color values cited in the detailed botanical description which accurately describe the colors of the new Rose.

The photograph at the top of the sheet comprises a side perspective view of a typical plant of 'Evera160' grown in a container.

The photograph at the bottom of the sheet is a close-up view of a typical flower of 'Evera160'.

DETAILED BOTANICAL DESCRIPTION

The new Rose has not been observed under all possible environmental conditions. The phenotype may vary somewhat with variations in environment such as temperature and light intensity, without, however, any variance in genotype. The aforementioned photographs, following observations and measurements describe plants grown during the autumn and winter in Fåborg, Denmark, in a glass-covered greenhouse and under commercial production practices. Plants were pinched one time and were about 12 to 14 weeks old when the photographs and description were taken. During the production of the plants, day temperatures averaged 22° C., night temperatures averaged 21° C. and light levels were about 20,000 lux. Three cuttings were grown in 10-cm containers. Plants used in the description represent a single plant. In the following description, color references are made to The Royal Horticultural Society Colour Chart, 2001 Edition, except where general terms of ordinary dictionary significance are used.

Botanical classification: *Rosa hybrida* cultivar Evera160.

Parentage:

*Female, or seed, parent.*—Proprietary seedling selection of *Rosa hybrida* identified as code number 03-0906, not patented.

*Male, or pollen, parent.*—Unnamed selection of *Rosa hybrida,* not patented.

Propagation:

*Type.*—By cuttings.

*Time to initiate roots.*—About ten to twelve days at 24° C.

*Time to produce a rooted young plant.*—About four weeks at 24° C.

*Root description.*—Fibrous, fleshy, medium thickness; white in color.

*Rooting habit.*—Freely branching; moderately dense.

Plant description:

*Plant form.*—Upright and rounded plant habit.

*Growth habit.*—Moderately vigorous. Freely branching habit; about three lateral branches develop from the pinch; dense and bushy growth habit.

*Plant habit.*—About 18 cm to 20 cm.

*Plant width* (*spread*).—About 15 cm to 24 cm.

*Lateral branches.*—Length: About 16 cm to 19 cm. Diameter: About 3 mm. Internode length: About 1 cm to 1.5 cm. Strength: Strong. Texture: Smooth, glabrous. Color: Between 144A and 146B. Thorns: Density: None to about three per linear cm. Shape: Triangular with sharp acuminate apices. Height: About 3 mm to 5 mm. Diameter, at base: About 1.5 mm to 2 mm. Color, immature: Close to 151A. Color, mature: Close to 152C to 152D.

Foliage description:

*Arrangement.*—Alternate; compound with three to five leaflets per leaf.

*Leaf length.*—About 9 cm to 10 cm.

*Terminal leaflet length.*—About 4.5 cm to 5 cm.

*Lateral leaflet length.*—About 2 cm to 4 cm.

*Leaf width.*—About 7 cm to 8 cm.

*Terminal leaflet width.*—About 3 cm to 3.5 cm.

*Lateral leaflet width.*—About 1.8 cm to 3 cm.

*Leaflet shape.*—Ovate.

*Leaflet apex.*—Acuminate.

*Leaflet base.*—Obtuse.

*Leaflet margin.*—Serrulate.

*Leaflet texture, upper and lower surfaces.*—Smooth, glabrous; leathery.

*Leaflet venation pattern.*—Pinnate; reticulate.

*Leaflet color.*—Developing leaflets, upper surface: Close to 137C. Developing leaflets, lower surface: Close to 148B tinted slightly with close to 59A. Fully developed, upper surface: Darker than 147A; venation, close to 146B. Fully developed, lower surface: Darker than 191A; venation, close to 146C.

*Petioles.*—Leaf petiole length: About 1.5 cm to 2.54 cm. Leaflet petiole length: About 2 mm to 3 mm. Leaf petiole diameter: About 1 mm. Leaflet petiole diameter: About 1 mm. Leaf petiole texture, upper and lower surfaces: Glabrous; rough. Leaflet petiole texture, upper and lower surfaces: Smooth, glabrous. Leaf petiole color, upper surface: Darker than 146A. Leaf petiole color, lower surface: Darker than 144A. Leaflet petiole color, upper surface: Close to 146B. Leaflet petiole color, lower surface: Close to 146C.

*Stipules.*—Quantity: Two per leaf. Length: About 1.3 cm to 1.5 cm. Width: About 2 mm. Shape: Lanceolate. Apex: Acuminate. Base: Truncate; sessile. Margin: Irregularly serrate. Texture, upper and lower surfaces: Smooth, glabrous; leathery. Color, upper surface: Close to 137A. Color, lower surface: Close to 137C.

Flower description:

*Flower type and habit.*—Large double orange-colored flowers with numerous petals. Consistently symmetrical rosette flowers. Flowers borne singly on erect and strong peduncles; one terminal flower per lateral branch. Flowers persistent.

*Flowering season.*—Year-round under greenhouse conditions, optimal flowering from spring through autumn under garden conditions; flowering intermittent. Plants begin flowering about 78 days after planting.

*Flower diameter.*—About 4 cm to 5 cm.

*Flower depth* (*height*).—About 3 cm.

*Flower longevity on plant.*—About two weeks.

*Fragrance.*—None detected.

*Flower buds* (*at stage of showing color*).—Shape: Ovoid. Length: About 1 cm. Diameter: About 9 mm. Color: Close to 137C.

*Petals.*—Quantity: Numerous; about 65 per flower arranged in numerous whorls. Length: About 2.8 cm to 3.2 cm. Width: About 3 cm to 3.4 cm. Shape: Broadly obovate. Apex: Acute. Base: Attenuate. Margin: Entire. Texture, upper and lower surfaces: Smooth, glabrous; satiny. Color: When opening, upper surface: Close to 37A; towards the margin, 31B to 31C; towards the base, 5B. When opening, lower surface: Close to 51B; spot at base, close to 1C to 1D. Fully opened, upper surface: Close to 31B; towards the base, 7A; with development, close to 31C. Fully opened, lower surface: Close to 39B; towards the base, close to 4C.

*Sepals.*—Quantity per flower: Typically five. Length: About 3 cm to 3.5 cm. Width: About 7 mm. Shape: Lanceolate. Apex: Sharply pointed. Base: Truncate. Texture, upper and lower surfaces: Pubescent; leathery. Color: When opening, upper surface: Close to 146B. When opening, lower surface: Close to 144A. Fully expanded, upper surface: Close to 146A. Fully expanded, lower surface: Close to 137C.

*Peduncles.*—Strength: Strong; flexible. Aspect: Mostly erect. Length: About 3.5 cm to 4.5 cm. Diameter:

About 2.5 mm to 3.5 mm. Texture: Rough. Color: Darker than 144A.

*Reproductive organs.*—Stamens: Quantity: About 85 per flower. Anther length: About 2 mm. Anther shape: Reniform. Anther color: Close to 17C. Filament color: Close to 17A. Pollen amount: None observed. Pistils: Quantity; About 60 per flower. Pistil length: About 2 mm to 4 mm. Stigma color: Close to 5A. Style length: About 3 mm to 6 mm. Style color: Close to 5D. Receptacle shape: Funnel-shaped. Receptacle height: About 8 mm. Receptacle diameter: About 9 mm. Receptacle texture: Smooth, glabrous. Receptacle color: Darker than 144A. Seed/fruit: Seed and fruit production has not been observed.

Pathogen/pest resistance: Plants of the new Rose have not been observed to be resistant to pathogens and pests common to Roses.

It is claimed:

1. A new and distinct Rose plant named 'Evera160' as illustrated and described.

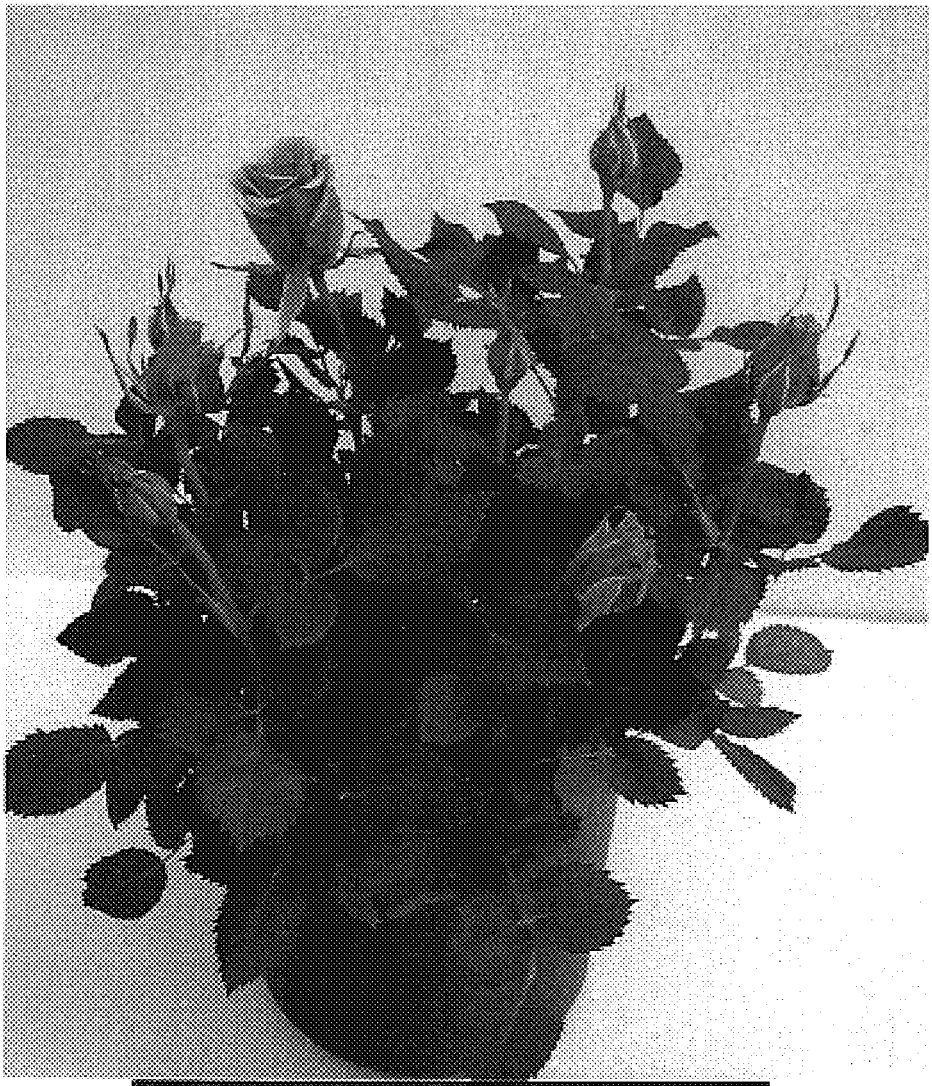
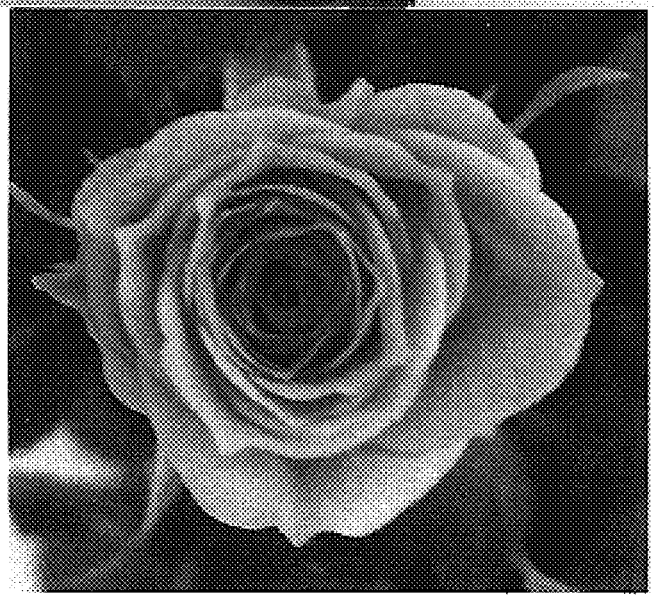

* * * * *